(12) United States Patent
Hirata et al.

(10) Patent No.: US 9,078,962 B2
(45) Date of Patent: Jul. 14, 2015

(54) BREAST PUMP

(75) Inventors: Naoko Hirata, Tokyo (JP); Satoru Saito, Tokyo (JP); Daisuke Yamashita, Tokyo (JP); Mitsuo Tashiro, Tokyo (JP)

(73) Assignee: Pigeon Corporation, Tokyo (JP)

( * ) Notice: Subject to any disclaimer, the term of this patent is extended or adjusted under 35 U.S.C. 154(b) by 0 days.

(21) Appl. No.: 14/113,657

(22) PCT Filed: Apr. 25, 2012

(86) PCT No.: PCT/JP2012/002844
§ 371 (c)(1),
(2), (4) Date: Dec. 19, 2013

(87) PCT Pub. No.: WO2012/147345
PCT Pub. Date: Nov. 1, 2012

(65) Prior Publication Data
US 2014/0094747 A1    Apr. 3, 2014

(30) Foreign Application Priority Data
Apr. 28, 2011   (JP) .................................. 2011-101832

(51) Int. Cl.
*A61M 1/06* (2006.01)
*A61M 1/00* (2006.01)

(52) U.S. Cl.
CPC ............... *A61M 1/06* (2013.01); *A61M 1/0072* (2014.02); *A61M 1/064* (2014.02); *A61M 1/066* (2014.02)

(58) Field of Classification Search
CPC ........ A61M 1/06; A61M 1/064; A61M 1/066
USPC .............................. 604/73–76, 346
See application file for complete search history.

(56) References Cited

U.S. PATENT DOCUMENTS 6,579,258 B1    6/2003  Atkin et al.
6,673,037 B1 *  1/2004  Silver .............................. 604/74

(Continued)

FOREIGN PATENT DOCUMENTS

| FR | 1067421 A | 12/1952 |
|----|-----------|---------|
| FR | 1067421 A | 6/1954 |
| JP | 2005-502397 A | 1/2005 |
| JP | 2008-194083 A | 8/2008 |
| JP | 4413231 B2 | 2/2010 |
| JP | 4467498 B2 | 5/2010 |
| JP | 2010-148885 A | 7/2010 |

OTHER PUBLICATIONS

International Search Report for PCT Patent App. No. PCT/JP2012/002844 (May 22, 2012).
Office Action from Japanese Patent App. No. 2011-101832 (Dec. 17, 2014).

*Primary Examiner* — Theodore Stigell
*Assistant Examiner* — Amber Stiles
(74) *Attorney, Agent, or Firm* — Cermak Nakajima & McGowan LLP; Tomoko Nakajima

(57) ABSTRACT

The invention provides a breast pump capable of effectively preventing the occurrence of leaking of breast milk from a milk expressing section having an enlarged diameter during expression of milk, and also effectively preventing the loss of negative pressure due to leaking. A breast pump has an accommodating vessel for collecting breast milk; a breast pump main body which generates negative pressure for expressing milk; an enlarged-diameter milk expressing section having an enlarged diameter for abutting against a breast of a user; and a shock absorbing section, at least a portion of which abuts against a breast of a user by being formed in a substantially circular trumpet shape following an opening section of the enlarged-diameter milk expressing section, wherein the shock absorbing section includes an abutting section which abuts against an areola of the user and a tight contact section which makes tight contact with the user's breast.

16 Claims, 7 Drawing Sheets

(56) References Cited

U.S. PATENT DOCUMENTS

| | | |
|---|---|---|
| 7,749,188 B2 | 7/2010 | Tashiro et al. |
| 2002/0198489 A1 | 12/2002 | Silver et al. |
| 2005/0245860 A1* | 11/2005 | Britto et al. ............... 604/74 |
| 2007/0078383 A1 | 4/2007 | Tashiro et al. |
| 2008/0195039 A1 | 8/2008 | Kataoka et al. |
| 2010/0121267 A1* | 5/2010 | Silver et al. ............... 604/74 |
| 2010/0130921 A1* | 5/2010 | Kobayashi et al. ......... 604/74 |
| 2011/0071466 A1 | 3/2011 | Silver et al. |
| 2012/0004604 A1* | 1/2012 | Van Der Kamp et al. .... 604/74 |

\* cited by examiner

F I G. 5
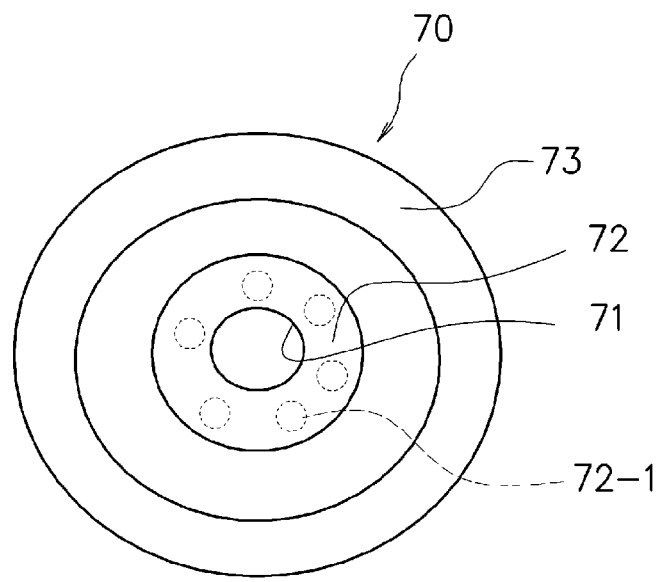
F I G. 6
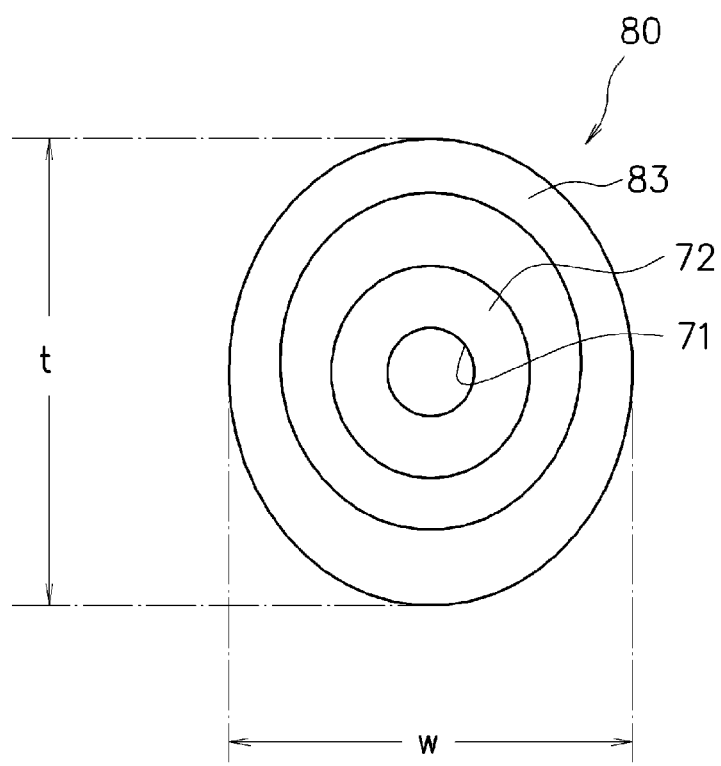

F I G. 7
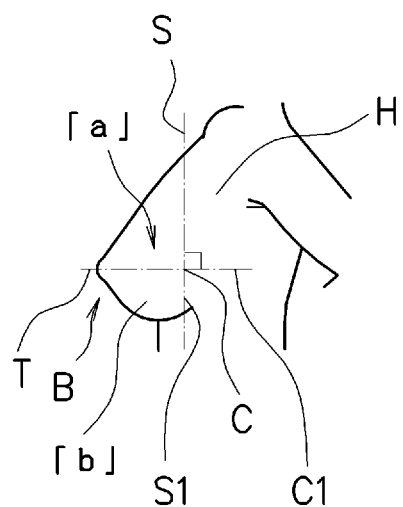
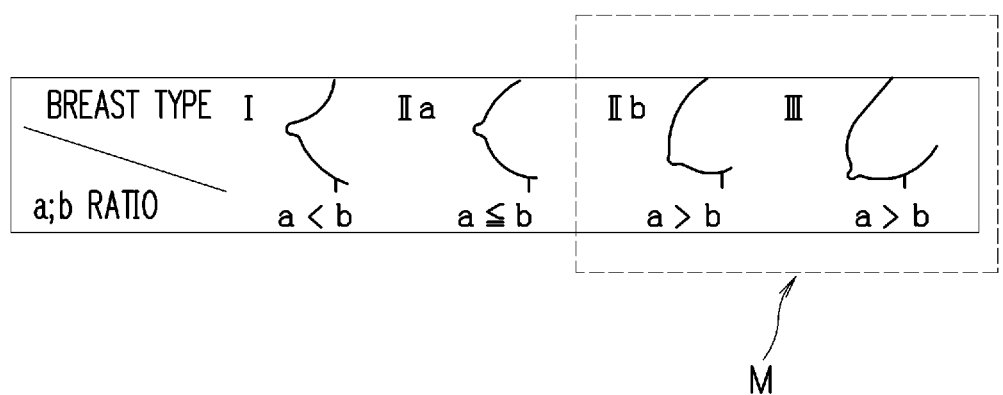

BREAST PUMP

This application is a national phase entry under 35 U.S.C. §371 of PCT Patent Application No. PCT/JP2012/002844, filed on Apr. 25, 2012, which claims priority under 35 U.S.C. §119 to Japanese Patent Application No. 2011-101832, filed Apr. 28, 2011, both of which are incorporated by reference.

TECHNICAL FIELD

This invention relates to improvement of a breast pump which suctions a user's breast by generating a negative pressure in order to express milk.

BACKGROUND ART

A breast pump provided with a milk expressing section having a diameter enlarged into a trumpet shape which is abutted against a mother's breast, in other words, an enlarged-diameter milk expressing section, is used widely.

In particular, a composition is known in which a recess is provided on an upper end, or the like, of a breast pump main body, in such a manner that breast milk which has turned into a mist due to the negative pressure during expression of milk does not leak out externally, and a deforming member, such as a diaphragm, is accommodated inside this recess.

In other words, a manual breast pump is known in which an operating section such as a handle, is coupled to a diaphragm, and a negative pressure is created by repeatedly lifting up the diaphragm by reciprocal movement of the handle; the breast pump relating to Japanese Patent No. 4413231 presented by the present applicants is one manual breast pump of this kind (Patent Document 1).

The breast pump according to Patent Document 1 can be disassembled and assembled easily for cleaning, but the operating section cannot been removed easily when operated.

Hence, in this breast pump, a shock absorber 28, which is an elastic body, is detachably attached on the inside of a trumpet-shaped enlarged-diameter milk expressing section 22.

This shock absorber 28 is provided to reduce stimulus caused by the abutment of a breast against the milk expressing section 22 during expressing milk and also to prevent pain arising therefrom.

CITATION LIST

Patent Literature

Patent Document 1: Japanese Patent No. 4413231

SUMMARY OF INVENTION

Technical Problem

However, since the trumpet-shaped enlarged-diameter milk expressing section is made from hard synthetic resin, or the like, then a conventional shocking absorbing section hardly serves any positive purpose beyond that of preventing uncomfortable stimulus or pain by being interposed between the milk expressing section and the user's breast during the expression of milk.

As described below, users of a breast pump have breasts of various different sizes and shapes, depending on the person.

Therefore, there is a problem in that breast milk may leak out from the milk expressing section during the expression of milk, due to the shape of the breast.

Furthermore, since there has been virtually no modification to the physical action, apart from suctioning by a negative pressure generated by the milk expressing section main body, then further improvement in milk expressing efficiency is also desired.

In this respect, a composition such as that shown in FIG. 13 is conceivable.

In FIG. 13, reference symbol B indicates a main portion of a breast (breast portion), and reference symbol K indicates a nipple. FIG. 13 shows a case where the breast pump is used by a woman having large breasts.

In FIG. 13, the breast B is received in a trumpet-shaped enlarged-diameter milk expressing section 1 and during expression of milk, the breast is suctioned by a negative pressure inside the enlarged-diameter milk expressing section 1.

In particular, in the case shown in FIG. 13, in order to prevent the problem described above, in other words, the causing of uncomfortable stimulus or pain to the user's breast due to the fact that the enlarged-diameter milk expressing section 1 is made from a hard synthetic resin, or the like, a shock absorbing cover 2 made from soft synthetic resin or rubber material, or the like, is provided through a broad range from the opening section of the enlarged-diameter milk expressing section 1 and over the entire inner surface thereof.

A through hole 5 is provided in the center of this shock absorbing cover 2, the nipple K enters into the through hole 5, and breast milk is guided inside the enlarged-diameter milk expressing section 1 and is sent to a collecting section, such as a bottle of the like, which is not illustrated.

In a composition of this kind, as shown in FIG. 13, in a state where the breast main portion B of the user is abutted against the enlarged-diameter milk expressing section 1 in a central part, the shock absorbing cover 2 makes tight contact with a broad range or region, continuously from the user's areola to the breast main portion B, as indicated by reference numeral 3. Therefore, not only the nipple K, but also the areola surrounding the nipple, and the skin of the breast main portion B, are suctioned strongly by the action of the negative pressure which acts during expression of milk, as indicated by arrow 6, and in addition to causing pain, there is also a drawback in that even if a large negative pressure is created, the milk expression efficiency does not become proportionately better.

This invention was devised in order to resolve the problem described above, and more particularly, an object thereof is to present a breast pump which can effectively prevent leaking of breast milk from the enlarged-diameter milk expressing section during expression of milk and loss of negative pressure due to leaking, without causing uncomfortable stimulus or pain to the user.

Solution to Problem

In order to achieve the abovementioned object, the present invention is a breast pump, having: an accommodating vessel for collecting breast milk; a breast pump main body which is attached to and detached from the accommodating vessel and which generates a negative pressure for expressing milk; and an enlarged-diameter milk expressing section which is provided on the breast pump main body and has an enlarged diameter in order to abut against a breast of a user, wherein a shock absorbing section is disposed attachably and detachably with respect to the enlarged-diameter milk expressing section, the shock absorbing section being devised in such a manner that at least a portion thereof abuts against a breast of a user by being formed in a substantially circular trumpet shape following an opening section of the enlarged-diameter milk expressing section; and the shock absorbing section includes: a through hole, in a central portion thereof, for exposing a nipple of a breast of a user in a state where the breast of the user is abutted against the enlarged-diameter milk expressing section; an areola abutting section which is a protrusion-shaped or concentric circle-shaped projecting section provided at a position in the vicinity of and on the outer side of the through hole and which abuts against the areola of the user; and a breast tight contact section which is a concentric circle-shaped projecting section provided in a position on the outer side of the areola abutting section and which makes tight contact with the breast of the user.

According to the composition described above, when a user abuts her own breast against the enlarged-diameter milk expressing section during expression of milk, the projecting breast is received inside the shock absorbing section. In this state, the areola abutting section abuts against the areola which is at the front end of the breast, and breast milk is suctioned out by the suctioning force created by negative pressure, in addition to which the areola abutting section presses effectively on the areola thereby facilitating the outflow of milk.

In this state, the breast tight contact section abuts tightly and forms a seal in a planar shape against the breast, and more specifically, a region located to the outside of the areola, apart from the areola, thereby preventing external leaking of the negative pressure, as well as effectively preventing external leaking of breast milk.

Desirably, the shock absorbing section has a substantially longitudinally elliptical trumpet shape following an opening section of the enlarged-diameter milk expressing section.

According to the composition described above, if the user has relatively large breasts, then the surface area of tight contact along the longitudinal direction is large, and therefore tight contact properties are improved and leaking of breast milk can be prevented effectively.

Desirably, on the shock absorbing section a cover section is provided which extends on the outer side at least along a lower side outer edge portion of the shock absorbing section.

According to the composition described above, since leaking of breast milk often occurs during expression of milk due to milk dropping down around the lower edge or the lower side of the breast, then if a cover section is provided, it is effective to adopt a cover section which extends along the lower side outer edge portion of the shock absorbing section so as to cover at least the region in question.

Desirably, a cover portion which extends in a ring shape along the outer edge portion is provided on the shock absorbing section.

According to the composition described above, by forming a cover portion in a ring shape through the whole circumference along the outer edge of the shock absorbing section, it is possible to cover the breast through a broader range, and therefore leaking of breast milk during expression of milk can be prevented more reliably.

Desirably, the areola abutting section is constituted by projections which abut against a plurality of locations on the areola of the user, in the vicinity of and on the outer side of the through hole.

According to the composition described above, since the areola abutting section is formed as projections which project at a plurality of locations, rather than projecting in a ring shape in the vicinity of and on the outer side of the through hole, then it is possible to apply pressure reliably to the user's areola at a plurality of locations during expression of milk, and therefore a stimulus for improving the outflow of breast milk can be applied effectively.

BRIEF DESCRIPTION OF DRAWINGS

FIG. 5 is a schematic front surface diagram of the shock absorbing section in FIG. 3;

FIG. 6 is a schematic front surface diagram showing a second embodiment of the shock absorbing section in FIG. 3;

FIG. 7 is a diagram showing a schematic view of types of breast size and breast shape of a person using the breast pump;

DESCRIPTION OF EMBODIMENTS

Below, preferred embodiments of the invention are described in detail with reference to the accompanying drawings.

The embodiments given below are preferred concrete examples of the present invention, and therefore although various technically desirable limitations are indicated, the range of the present invention is not limited to these modes, unless it is explicitly stated in the description given below that the invention is limited.

Figure 1:
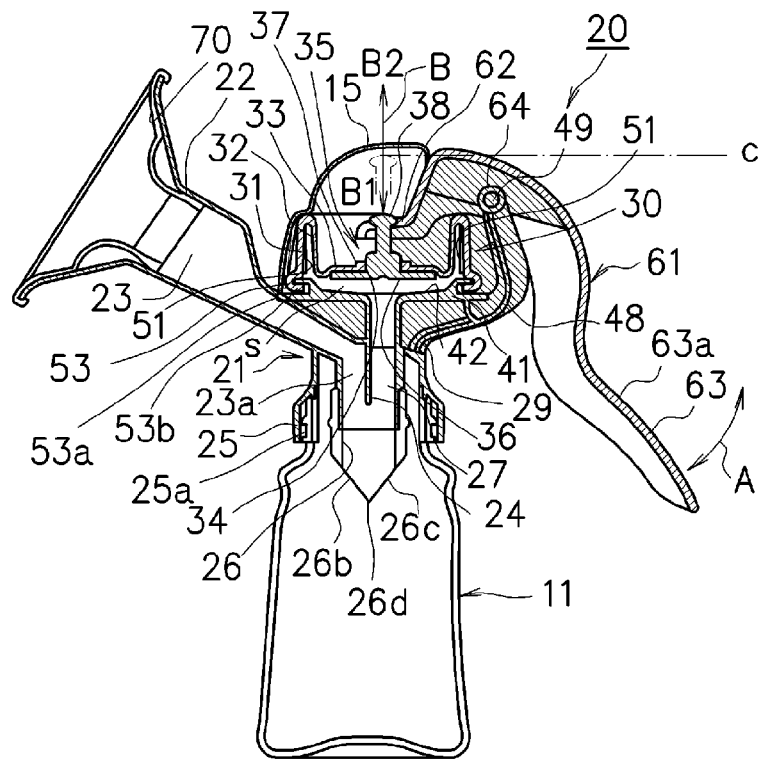
FIG. 1 is a schematic cross-sectional diagram of a breast pump relating to an embodiment of the present invention.
Figure 2:
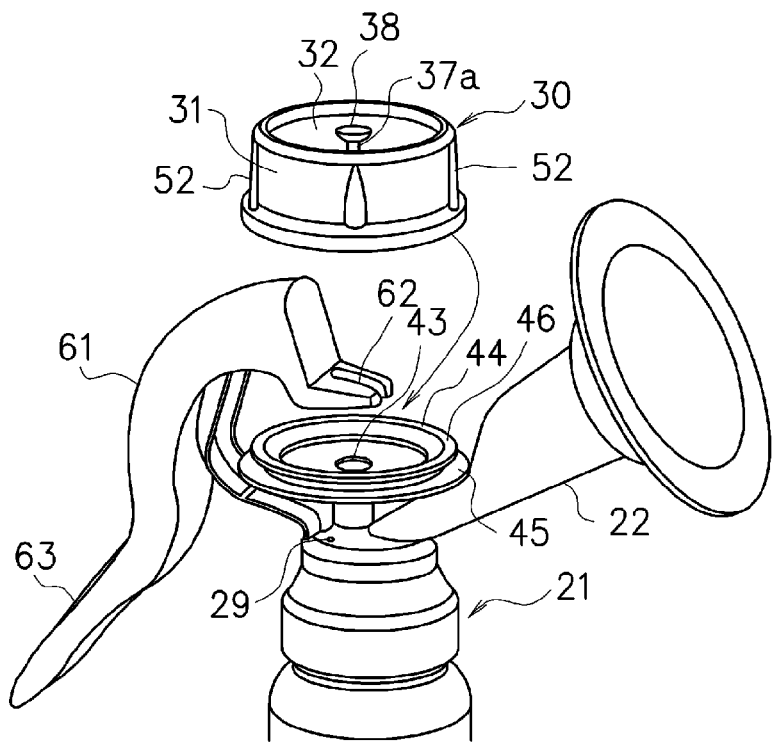
FIG. 2 is an exploded perspective diagram showing a structure of an upper portion of the breast pump in FIG. 1.

FIG. 1 and FIG. 2 show a general schematic composition that is common to each of the embodiments of the present invention. FIG. 1 is a schematic cross-sectional diagram of an embodiment, and FIG. 2 is an exploded perspective drawing of a cross portion thereof. In these drawings, the structure of the shock absorbing section is shown for reference purposes, and the details are shown in other drawings.

In FIG. 1 and FIG. 2, the breast pump 20 comprises a breast pump main body 21 (called "main body" below), a handle 61, which is an operating device, and a bottle 11 as an accommodating vessel for collecting the expressed breast milk. The handle 61 can be attached to and detached from the breast pump main body 21.

Furthermore, as shown in FIG. 1, a substantially dome-shaped hood 15 can be attached to and detached from an upper section of the main body 21 where a negative pressure generating member 30 is installed.

As can be seen by reference to FIG. 1, the hood 15 is cut out in the location of the handle 61 and can cover and protect the negative pressure generating member 30, or the like, by being fitted so as to avoid the handle 61. It is also possible to adopt a composition which does not include the hood 15.

Moreover, in this embodiment, a composition is adopted in which a negative pressure is created manually, but it is also possible to create a negative pressure by using an electric motor, or the like, as implemented widely.

The whole of the main body 21 is made from synthetic resin material which is relatively light and robust; for example, the main body 21 is made from polypropylene, polycarbonate, polycyclo-olefin, polyether sulfone, polyphenyl sulfone, or the like.

The main body 21 is provided with an attachment and detachment section 25 for attaching to and detaching from the bottle 11. The attachment and detachment section 25 is, for example, a flat tubular portion as shown in FIG. 1, which has a female thread section 25a on the inner side, so as to threadedly engage with a male thread section formed on the circumference of a mouth of the bottle 11.

The bottle 11 may be a product specially made for the breast pump 20 or may use a feeding bottle which is compatible with the attachment and detachment section 25, or may be a bag-shaped member, rather than a formed vessel.

A conical or trumpet-shaped enlarged-diameter milk expressing section 22 having a front end which opens to a large diameter is provided in an obliquely inclined state on top of the attachment and detachment section 25 of the main body 21. A shock absorbing section 70, which is an elastic body, is attached detachably to the opening side of the enlarged-diameter milk expressing section 22.

The shock absorbing section 70 reduces the stimulus produced when the enlarged-diameter milk expressing section 22 abuts against the breast during expression of milk, so as not to cause pain. The structure of the shock absorbing section 70 is desirably different to FIG. 1, and is described in detail hereinafter.

The milk expressing section air flow path 23 of the enlarged-diameter milk expressing section 22 is a flow path for air and expressed breast milk, which bends downwards towards the bottle 11. Furthermore, the opening of the milk expressing section air flow path 23 of the enlarged-diameter milk expressing section 22 is located on the inner side of the attachment and detachment section 25 between the main body 21 and the bottle 11, and a small chamber 26 is attached thereto. Moreover, a further air flow path 27 is provided via a partition wall 24, adjacently to a downward facing portion 23a of the milk expressing section air flow path 23. As shown in the figures, the lower end opening of the air flow path 27 communicates with the downward facing portion 23a of the milk expressing section air flow path inside the small chamber 26.

The upper end of the air flow path 27 has an opening 43, as shown in FIG. 2, and is formed into a mounting section 41 which enlarges in a substantially circular shape so as to surround the opening 43. The mounting section 41 is a portion where the negative pressure generating member 30 is installed. The negative pressure generating member 30 is described in detail below.

The upper surface of this mounting section 41 is formed as an inclined surface 42 which is inclined so as to descend slightly towards the opening 43.

As shown in FIG. 1, the small chamber 26 is a hollow cup-shaped member which is made entirely from an elastic body of silicone rubber, an elastomer, natural rubber, or the like, and both side walls 26b, 26c on the lower end side thereof are valve elements which constitute inclined walls of the elastic body that are formed to a small thickness and gradually approach each other towards the lower end. A slit 26d is provided on the lower end where the two side walls 26b, 26c approach each other, and when a prescribed amount of expressed breast milk has been collected inside the small chamber 26, then due to the weight of the collected milk and the change in pressure when the negative pressure is released, as described below, the slit 26d opens, and the breast milk drops down inside the bottle 11. Furthermore, since a slit 26d is formed at the lower end of the inclined walls, then when negative pressure is applied, the air inside the bottle 11 is prevented from entering into the small chamber 26.

Moreover, a small ventilation hole 29 which communicates the interior of the bottle 11 with the outside air is formed at a location adjacent to the attachment and detachment section 25 of the breast pump main body 21, so that pressure occurring when the breast milk has collected inside the bottle 11 can escape.

The negative pressure generating member 30 has an overall form close to that of a relatively flat round cylindrical body having a bottom.

More specifically, as shown in FIG. 1, the negative pressure generating member 30 has a first wall section 31 which is erected on an outer side and provides sufficient rigidity to maintain the outer diameter, and a second wall section 32 which is an inside wall section of which the upper end portion is bent back to the inner side in an integrated fashion, and the portion forward of the bent back portion is formed with a small thickness. The second wall section 32 is a deforming section, the lower end of which forms a bottom surface section 33, which is a relatively broad inner bottom section provided to extend in an integrated fashion so as to close off the lower portion of the round cylindrical shape.

In other words, the first wall section 31 and the second wall section 32 are made from the same material, but different rigidities are imparted by varying the thickness of the material, in such a manner that the first wall section 31 does not deform but the second wall section 32 can deform, the second wall section 32 being disposed along the first wall section 31 so as to ensure a prescribed negative pressure, as described hereinafter.

In the negative pressure generating member 30, due to the operation of the handle 61, as described hereinafter, the second wall section 32, which is the deforming section, deforms and the volume of the internal space S formed between the bottom surface section 33 and the mounting section 41 changes, thereby making it possible to create a negative pressure by suctioning air inside the milk expressing section air flow path 23 which is communicated with the internal space S via the air flow path 27 and the small chamber 26 (see FIG. 1).

In this case, the wall section, in other words, the first wall section 31 hardly deforms at all, and hence the state of installation with respect to the mounting section 41 can be maintained.

Desirably, as shown in FIG. 2, reinforcing ribs 52 extending in the longitudinal direction are formed on an outer surface of the first wall section 31, thereby further enhancing the function of maintaining the shape of the wall.

Furthermore, as shown in FIG. 1, longitudinal ribs 51 extending in the longitudinal direction are provided on the opposing surfaces of the first wall section 31 and the second wall section 32, which is the deforming section, so as to be interposed between these wall sections. Here, the longitudinal ribs 51 are formed on the inner surface side of the first wall section 31. When the second wall section 32, which is the deforming section, repeatedly deforms and then is restored to its original shape, during this restoring motion, an operating sound is produced when the opposing surfaces of the second wall section 32 and the first wall section 31 abut against each other, but the presence of the longitudinal ribs 51 effectively prevents this sound from becoming an unpleasant sound.

In order to deform the second wall section 32, which is a deforming section, a coupling section (member) 35 is provided.

The coupling section (member) 35 is made from a hard material which is different to the second wall section 32, which is a deforming section. The coupling section (member) 35 is made entirely from a relatively hard synthetic resin, such as polypropylene, polycarbonate, polycyclo-olefin, polyether sulfone, or the like, and has a flat circular disk-shaped base section 36 of which the base end section is enlarged to a broad diameter. Furthermore, in FIG. 1, the coupling section (member) 35 has a boss section 37 erected to a low height, which is formed in an integrated fashion on top of the base section 36 and has a sufficiently large outer diameter to impart strength, and an extending section 37a which extends in a relatively narrow shape from the boss 37. Moreover, an engaging section 38, which is a protruding section or enlarged-diameter section having a circular, elliptical or oval cross-sectional shape, or the like, is provided on a front end of the extending section 37a.

A through hole or a clearance hole 34 is formed in a central portion of the bottom surface section 33.

More specifically, if the negative pressure generating member 30 and the coupling member 35 are formed as separate bodies, then reference numeral 34 is a clearance hole, and by setting the clearance hole 34 to have a slightly smaller internal diameter than the external diameter of the boss section 37 and by inserting the boss section 37 from the rear surface of the bottom surface section 33, attachment can be performed very easily, while reliably ensuring airtight properties. In this case, detachment for the purpose of cleaning, or the like, can also be performed easily.

On the other hand, it is also possible to join the coupling section 35 with the bottom surface section 33 and the through hole 34 by using two-part molding or insert molding. In this case, the manufacturing costs become correspondingly higher, but since the hole of the negative pressure generating member 30 is a single integrated component, handling becomes easier.

As shown in FIG. 1, the negative pressure generating member 30 having the constitution explained above is attached to and detached from a peripheral edge section of the mounting section 41, by an attachment and detachment section 53 which is formed in a substantially circular shape, the peripheral edge section being formed with a diameter slightly larger than the attachment and detachment section 53.

In FIG. 1 and FIG. 2, the attachment and detachment section 53 of the negative pressure generating member 30 has an inward facing flange 53a, which is a negative pressure generating side flange section that projects inwards at the lower end thereof, by the first wall section 31 extending downwards and being bent inwards, and an inner groove 53b which is a negative pressure generating side groove section which is formed on the upper side and the inner side of the flange 53a. The whole of the attachment and detachment section 53 has a prescribed rubber-like elasticity.

On the other hand, an outward facing dual flange is formed on the peripheral edge section of the mounting section 41. More specifically, the mounting section 41 is provided with a first flange 44, which is an outwardly projecting main body side flange section on the upper end of the mounting section 41 and a second flange 45 which is a positioning device positioned below the first flange 44 and having an outer diameter larger than the lower end of the attachment and detachment section 53 and the first flange 44, and furthermore an outer groove 46 which is open on the outer side is formed, this outer groove 46 being a main body side groove section that is indented to the inner side by reducing the diameter in the gap between the first flange 44 and the second flange 45.

A user grips the side surfaces constituted by the first wall section 31 and the second wall section 32 of the negative pressure generating member 30, and causes the outer surface of the inward facing flange 53a, which is the lower end of the attachment and detachment section 53 positioned on the opposite side to the gripped position, to abut against an upward facing step section of the second flange 45, which is a positioning device. In a state where the inward facing flange 53a is engaged inside the outer groove 46, the user pulls and tenses the negative pressure generating member 30 with her gripping hand while lightly pressing down on the engaged position with a finger of the non-gripping hand. Consequently, the inward facing flange 53a in the portion other than the engaged position deforms and rides up over the first flange 44 and enters into the main body side groove section 46. In so doing, the whole of the attachment and detachment section 53 becomes installed on the peripheral edge section, the first flange 44 enters into the inner groove 53b, and furthermore, the inward facing flange 53a also enters into the outer groove 46, whereby an installation that remains hermetically sealed is achieved.

Consequently, the negative pressure generating member 30 is installed very easily. In other words, the second flange 45 is formed at a position which is distanced slightly further from the first flange 44 than the thickness of the inward facing flange 53a, and when the negative pressure generating member 30 is installed, the second flange 45 serves as a projecting rib that prevents the inward facing flange 53a from riding up over the outer groove 46.

Furthermore, when, conversely, the negative pressure generating member 30 is removed, by simply holding the first wall section 31 by hand and stretching outwards, the inward facing flange 53a is removed from the outer groove 46 and rides up over the first flange 44, and therefore removal can be performed very easily.

In the present embodiment, the second flange 45 has a similar shape to the first flange 44, but it may also be formed with a portion that project beyond the first flange 44, in a part thereof; for example, it is also possible to adopt a composition in which a cutaway is formed in a side edge so as to facilitate the action of pressing with the other finger.

Here, the first wall section 31, the second wall section 32 and the bottom surface section 33 of the negative pressure generating member 30 are desirably made entirely as a single body from a soft material having very good relative elasticity, in other words, a synthetic resin having a hardness of approximately HS30 to 70 as measured by an A-type durometer according to JIS-K6253 (ISO 7619), or an elastomer such as silicone rubber, isoprene rubber, or SEBS (styrene-ethylene-butylene-styrene), for example.

Moreover, desirably, the thickness of the material constituting the portion of the first wall section 31 is 1.5 mm to 3.0 mm, and the thickness of the material constituting the second wall section 32 is 1.0 mm to 2.5 mm.

If the hardness of the negative pressure generating member 30 is smaller than 30, then the deformation of the first wall section 31 and the generated negative pressure both become small. If the hardness exceeds 60, then the force required to operate the handle 61 as described below becomes large, and the operation for creating a negative pressure becomes very difficult.

If the thickness of the second wall section 32 is smaller than 1.0 mm, then the extension due to rubber elasticity upon deformation becomes larger, and the generated negative pressure becomes smaller. If the thickness exceeds 2.5 mm, then the force required to operate the handle 61 as described below becomes large, and the operation for creating a negative pressure becomes very difficult.

If the thickness of the first wall section 31 is smaller than 1.5 mm, then the wall section will buckle during the creation of a negative pressure. In other words, unwanted deformation occurs and a sufficient negative pressure cannot be generated. If the thickness of the first wall section 31 exceeds 3.0 mm, then the wall section cannot deform sufficiently during installation on the breast pump main body 21, and hence installation becomes difficult to perform.

As shown in FIG. 1 and FIG. 2, in the upper portion of the main body 21, an arm 48 for attaching the handle 61 extends at a position opposite to the position where the milk expressing section 22 extends. The arm 48 is located at a position whereby the front end thereof is adjacent to the negative pressure generating member 30 and is located above the upper end of the negative pressure generating member 30. In this embodiment, a horizontally disposed round cylindrical axle section 49 is provided on the front end of the arm 48.

The handle 61 is formed entirely as a molded part made as a single body from a light and relatively robust synthetic resin, for example, polypropylene, polycarbonate, polycycloolefin, polyether sulfone, and the like.

More specifically, as shown in FIG. 1, the handle 61 is a long member, having an engaged section 62 constituted by a cutaway in which the upper end is formed into two legs horizontally, and as shown in FIG. 2, the engaged section 62 can readily be attached to and detached from the engaging section 38 of the coupling section (member) 35. The other end 63 of the handle 61 is positioned on the lower side and projects slightly to the outside, as illustrated in FIG. 1, and has a lever-shaped external form overall.

The handle 61 is attached and detached with respect to the main body 21, and in the fixed state in FIG. 1, the handle 61 is installed rotatably, and can be attached to the axle 49 at the front end of the arm 48 by bearing sections 64 which are provided at a position towards one end of the handle 61.

A non-slip portion is formed on the outer side of the other end of the handle 61 by using an elastic material, or the like, and two-part molding, or the like, and by means of the operator holding and operating this position, the handle 61 performs a reciprocal movement of approaching and moving away from the bottle 11, as indicated by the arrow A in FIG. 2. The non-slip portion 63a does not have to be made from a different material, and it is possible to apply processing for raising the frictional force so to avoid slipping by providing undulations, such as bosses or ribs on the surface of the handle 61 at the corresponding location.

In accordance with this, the engaged section 62 at the front end of the handle 61 performs an upward and downward reciprocal motion as indicated by arrow B, by rotating about the axle section 49. When the user operates the handle 61 so as to approach the bottle 11 and the handle 61 moves in the direction of arrow B2, the second wall section 32 which is the deforming section of the negative pressure generating member 30 is deformed so as to face upwards from the downward facing state shown in FIG. 1. Therefore, when the volume of the internal space S formed between the bottom surface section 33 and the mounting section 41 is increased, air in the milk expressing section air flow path 23 is drawn in, in accordance with the amount of air drawn into the internal space S, and when a user's breast is abutted against the enlarged-diameter front end of the milk expressing section 22, a hermetic space is formed, and therefore the milk expressing section air flow path 23 assumes a negative pressure.

Due to this negative pressure, the expressed breast milk enters into the small chamber 26 from the downward facing portion 23a of the milk expressing section air flow path. A certain amount of breast milk collects in the small chamber 26. In this case, since the side walls 26b and 26c are formed thin, then the side walls 26b and 26c deform to some extent in a mutually approaching direction due to the negative pressure, so the slit 26d reliably assumes a hermetically sealed state and therefore the breast milk does not leak out.

When the user operates the handle 61 to a state of closest approach to the bottle 11, the upper end 62 moves to a limit position C, the inside end portion of the handle 61 abuts against the outer edge of a positioning section 45 opposing same, and the handle cannot be moved further. The second wall section 32, which is the deforming section, stops in an intermediately pulled-up state, and seeks to return in a direction toward the lower side in FIG. 1, which is the original shape thereof.

If the user loosens the force applied to the handle 61 from this state, then due to the force seeking to revert the second wall section 32, the upper end 62 moves in the direction of arrow B1, the handle 61 moves in a direction away from the bottle 11, and the second wall section 32, which is the deforming section of the negative pressure generating member 30, is restored to the state shown in FIG. 1. Therefore, the volume of the internal space S formed between the bottom surface section 33 and the mounting section 41 decreases, and due to the change in pressure caused by the release of the negative pressure, as well as the weight of the collected breast milk, the front end sides of the side walls 26b and 26c open, the slit 26d opens and breast milk drops down into the bottle 11.

By repeating the operation described above, with the operation of the handle 61, a negative pressure is applied in a pulsating fashion on the basis of the action of the negative pressure generating member 30, and milk is expressed.

According to the breast pump 20 described above, as the aforementioned description reveals, in the negative pressure generating member 30 which has an essential role in the expression of milk, the attachment and detachment section 53 which is attached to and detached from the mounting section 41 of the breast pump main body 21, the first wall section 31 which has sufficient rigidity to maintain the outer shape, and the second wall section 32, which is a deforming section, are formed entirely as a single body from resin having elastic properties.

Therefore, when the negative pressure generating member 30 is removed from the breast pump main body 21, there exists no recess section or depression created by the molding for accommodating the deforming section, in other words, the diaphragm, or the like, in the main body 21, as there is in a conventional breast pump.

Consequently, there is no collection of breast milk residue, or the like, inside a recess section that is difficult to clean, and the instrument does not become unhygienic. Since the negative pressure generating member 30 is made entirely from a soft material having elastic properties, then when the negative pressure generating member 30 is removed from the breast pump main body 21 for cleaning, if the operator presses a finger against the vicinity of the attachment and detachment section 53 and gently deforms same to the outer side, then the negative pressure generating member 30 can be removed easily, and once removed, can be cleaned easily and thoroughly due to being made entirely from a soft material.

Figure 3:
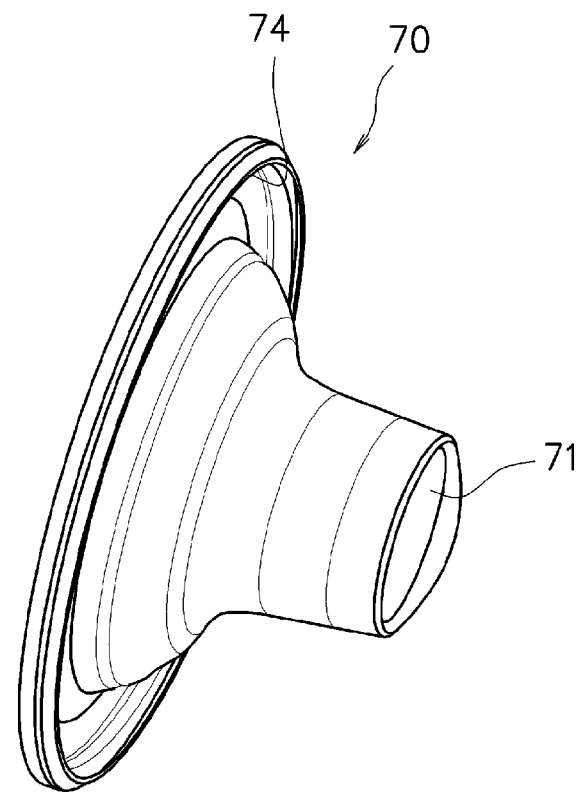
FIG. 3 is a side view diagram showing a first embodiment of a shock absorbing section which is attached to and detached from the enlarged-diameter milk expressing section of the breast pump in FIG. 1.

FIG. 3 is a side view diagram of the shock absorbing section 70 relating to a first embodiment.

In FIG. 3, the shock absorbing section 70 is formed as a single body from an elastic material, for example, a material which deforms easily and can readily make tight contact with the user's breast, such as silicone rubber, elastomer, natural rubber, or the like. For example, if silicone rubber is used, then a rubber having a JIS hardness from 20 to 80 approximately can be used.

Figure 4:
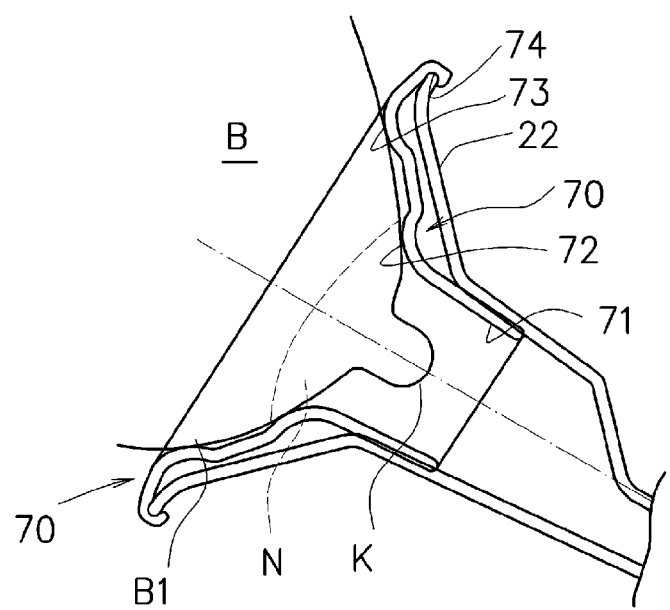
FIG. 4 is an enlarged cross-sectional diagram showing a relationship between the shock absorbing section in FIG. 3, a user's breast and the vicinity of the areola.

This shock absorbing section 70 has the cross-sectional shape shown in FIG. 4, and FIG. 5 shows a view thereof from the enlarged-diameter opening front surface. In FIG. 5, the dimensions of the respective parts are each different to FIG. 3, but FIG. 5 shows a schematic depiction of the shape and structure of the shock absorbing section as viewed from the front face, and does not depict a different structure.

In these drawings, on the side of the opening of the enlarged-diameter milk expressing section 22, the shock absorbing section 70 has a trumpet shape following the shape of the opening section, and is installed so as to enter inside this milk expression opening section.

In other words, the shock absorbing section 70 is an even trumpet shape which is open in one direction, and as can be seen clearly when referred to in conjunction with FIG. 3, has an even funnel shape overall.

More specifically, as shown in FIG. 4, the shock absorbing section 70 has a through hole 71, in a central part thereof, for exposing the nipple K inside a milk expressing path when the user's breast (main portion B) is abutted against the enlarged-diameter milk expressing section 22, an areola abutting section 72 which is constituted by a protrusion or concentric circle-shaped projecting sections provided at a position in the vicinity of the through hole 71 to the outer side thereof and which abuts against the areola N of the user, and a breast tight contacting section 73 which is constituted by concentric circle-shaped projecting sections provided at a position to the outer side of the areola abutting section 72 and which makes tight contact with the user's breast. An attachment section 74, which is in an open outer edge portion of the shock absorbing section 70, is formed by a narrow groove, and the shock absorbing section 70 is installed by fitting the outer edge of the enlarged-diameter milk expressing section 22 that opens in a trumpet shape into this groove.

Conversely, the shock absorbing section 70 can be removed from the enlarged-diameter milk expressing section 70 by turning this attachment section 74 outwards manually.

In other words, when the shock absorbing section 70 in FIG. 3 is installed on the breast pump 20 shown in FIG. 1, and the user abuts her own breast (main portion B) against the enlarged-diameter milk expressing section 22 for expression of milk (see FIG. 4), then the projecting breast is received inside the shock absorbing section 70. In this state, the areola abutting section 72 abuts against the areola N which is at the front end of the breast main portion B, and breast milk is sucked out by a suctioning pressure created by negative pressure, in addition to which the outflow of breast milk is improved due to the areola abutting section 72 pressing effectively against the areola N.

In this state, the breast tight contact section 73 abuts tightly and forms a seal in a planar shape against a region B1 of the breast located to the outside of the areola, apart from the areola, thereby preventing external leaking of the negative pressure, as well as effectively preventing external leaking of breast milk.

Here, as shown in FIG. 5, the areola abutting section 72 and the breast tight contact section 73 are both designed in a ring-shaped projecting state concentrically with the through hole 71, but the invention is not limited to this mode, and the areola abutting section 72 may also be composed in the form of protrusions 72-1 which abut against a plurality of locations on the user's areola N, in the vicinity of and on the outer side of the through hole 71.

In this case, since the areola abutting section 72-1 is formed as protrusions that project in a plurality of locations, rather than projecting in a ring shape in the vicinity of and on the outer side of the through hole 71, then pressure can be applied reliably to a plurality of locations on the user's areola N during the expression of milk, and it is therefore possible to apply a stimulus effectively in order to improve the outflow of milk.

FIG. 6 shows a shape of a shock absorbing section which is formed overall to a long dimension in the longitudinal direction, in a second embodiment of the invention.

More specifically, the shock absorbing section 80 is formed in such a manner that overall, the longitudinal dimension t is greater than the lateral dimension W.

Desirably, the through hole 71 is a perfect circular shape and the areola abutting section 72 is a perfect circular ring shape, and at least the breast abutting section 83 is an elliptical projection which is long in the longitudinal direction. Here, "longitudinal" means a direction following the body of the user when in use, and "lateral" means a direction following the width of the body.

In a case where the shock absorbing section 80 is formed as a substantially longitudinally elliptical trumpet shape following the opening section of the enlarged-diameter milk expressing section, as in the second embodiment in FIG. 6, if the main portion of the user's breast, namely, the breast main portion B, is relatively large, then the surface area of tight contact in the longitudinal direction will be large and hence the tight contact properties are improved and leaking of breast milk can be prevented effectively.

In this respect, the relationship between the breast size, and in particular the size of the breast main portion B, and the breast shape is described below.

FIG. 7 is cited from "Nyūbō kanrigaku" by Yahiro Netsu.

The left end part of FIG. 7 shows a schematic view of a female body H and the tip of the nipple of the breast is labeled T. Furthermore, the upper end portion of the breast on the front side of the body (the point where the breast starts) is labeled S, and a horizontal virtual line C1 passing through T and a perpendicular virtual line S1 passing through S are imagined. Of the breast regions divided by the two virtual lines C1 and S1, the upper side is labeled "a", and the lower side is labeled "b", and the table in the lower part of FIG. 7 is created. This table provides classifications relating to the breast size and breast shape.

The four breast forms (cross-sectional shapes) shown in the table in the lower part of FIG. 7 are termed "type I", "type IIa", "type IIb" and "type III", successively from the left side. In this series of breast forms, the b region is larger towards the left-hand side, and the a region is larger towards the right-hand side.

Of the breast types shown in FIG. 7, the beasts of type IIb and type III surrounded by the dotted line in the right end part are large pendulous breasts, in which the nipple points downwards.

Figure 8:
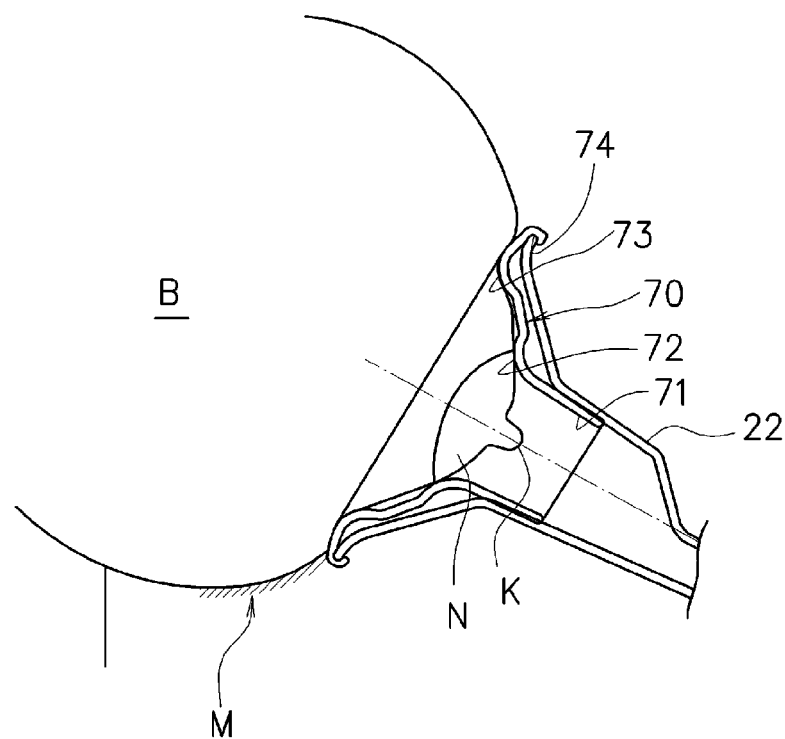
FIG. 8 is an enlarged cross-sectional diagram showing a relationship between the shock absorbing section and the user's breast and areola region during expression of milk, in the case of the shock absorbing section in FIG. 3.

With breasts of this kind, during expression of milk, problems such as that shown in FIG. 8 occur.

With a large swollen breast main portion B, as indicated by the reference symbol M in FIG. 8, leaking of breast milk as a result of inadequate tight contact with the breast tight contact section 73 of the shock absorbing section 70 often occurs, as milk drops from the outer edge of the shock absorbing section 70 and then around the lower edge or the lower side of the breast.

Figure 9:
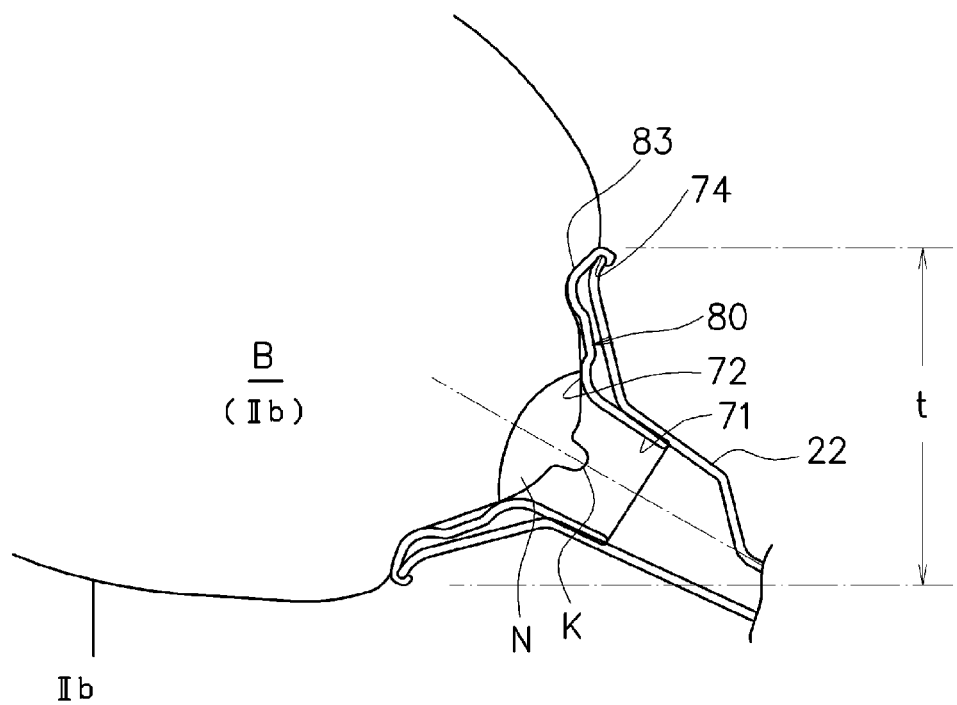
FIG. 9 is an enlarged cross-sectional diagram showing a state of using the second embodiment in accordance with the size and shape of the user's breast.
Figure 10:
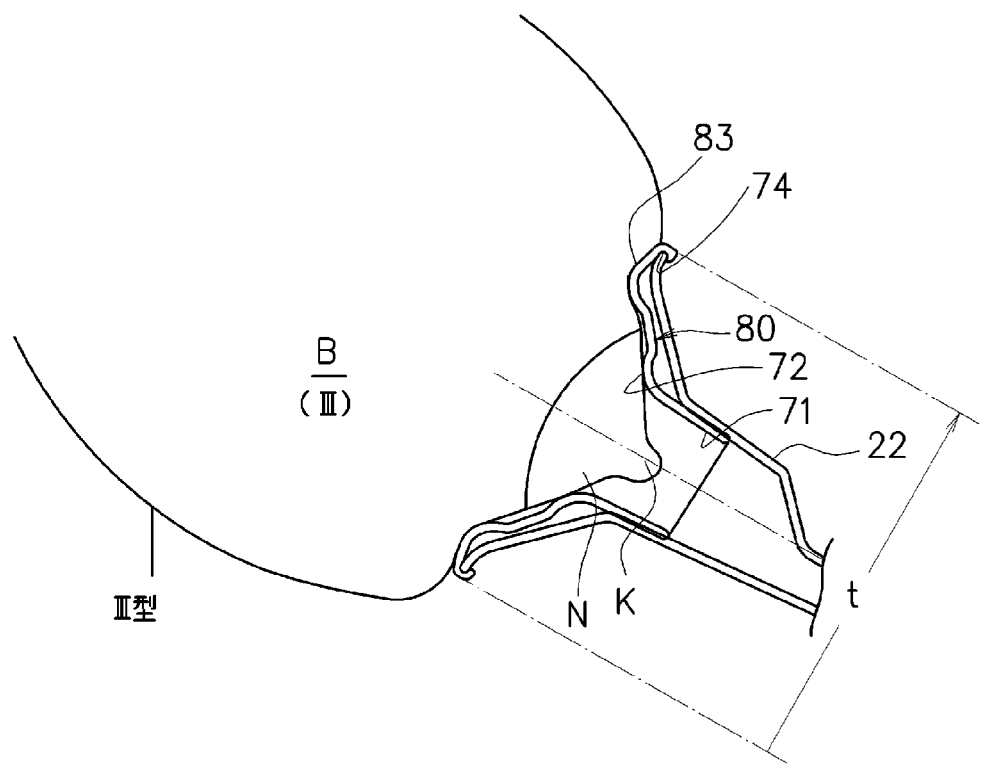
FIG. 10 is an enlarged cross-sectional diagram showing a state of using the second embodiment in accordance with the size and shape of the user's breast.

Therefore, as shown in FIG. 9 and FIG. 10, it is desirable to use a shock absorbing section 80 relating to the second embodiment as described in relation to FIG. 6. FIG. 9 and FIG. 10 shows states where a shock absorbing section 80 is used with a type IIb breast and a type III breast, respectively.

In other words, the shock absorbing section 80 is a longitudinally elliptical shock absorbing section which is long in the direction of dimension t, and the breast tight contact section 83 is long in the longitudinal direction.

As shown in these examples, in a case where the user has relatively large breasts, the shock absorbing section 80 yields a large surface area of tight contact along the longitudinal direction, and therefore the tight contact properties are improved and leaking of breast milk can be prevented effectively.

Figure 11:
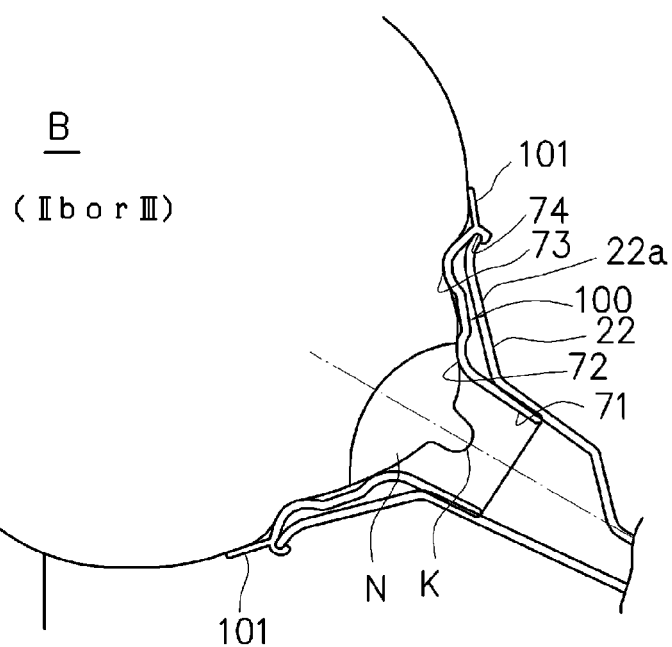
FIG. 11 is a schematic perspective diagram showing a third embodiment of the shock absorbing section in FIG. 3.

The shock absorbing section 100 in FIG. 11 relates to a third embodiment.

In FIG. 11, the shock absorbing section 100 attached to the enlarged-diameter milk expressing section 22 is provided with an outer edge cover section 101 which extends in an integrated fashion with an enlarged diameter in a ring-shape about the circumferential direction, to the outer side of the attachment section 74 which is the outer edge portion of the shock absorbing section 100.

The important point here is that the trumpet-shaped enlarged-diameter portion 22a of the enlarged-diameter milk expressing section 22 is of a sufficient size to adequately accommodate at least the spindle-shaped area which is the front end portion of the breast main portion B, and an outer edge cover section 101 of the shock absorbing section 100 is formed further to the outer side thereof. By adopting a structure of this kind, it is possible to achieve actions and effects such as those indicated below in the outer edge cover section 101.

Figure 13:
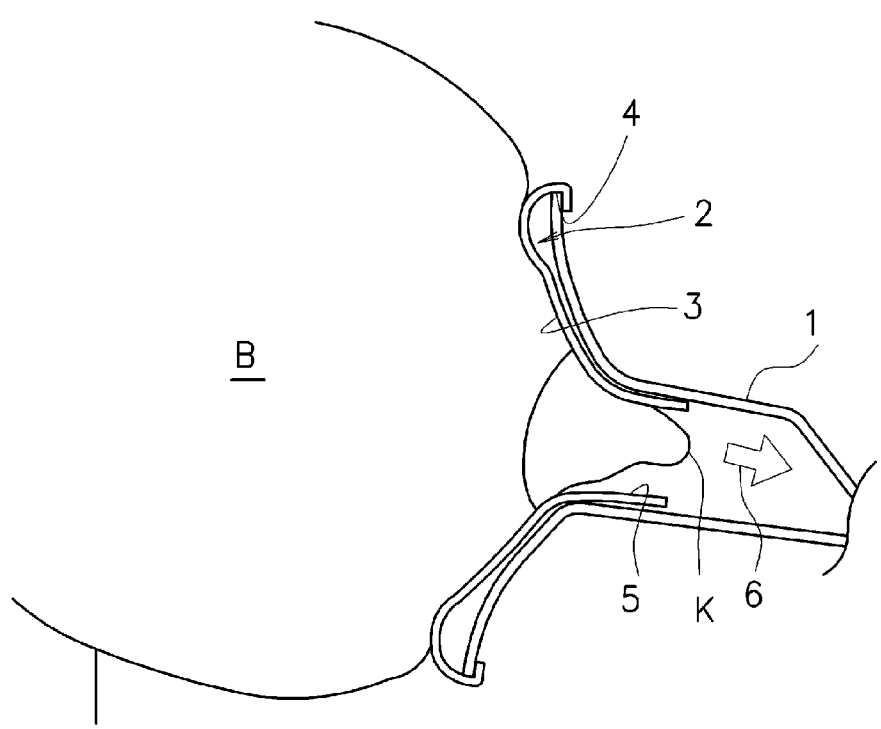
FIG. 13 is an illustrative diagram showing an example of a mode where a shock absorbing cover provided on the enlarged-diameter milk expressing section causes undesirable effects on the user.

As can be seen readily with reference to FIG. 11, by forming the outer edge cover section 101 in a ring shape throughout the whole circumference along the outer edge of the shock absorbing section 100, it is possible to cover the breast main portion B through a broader range. Therefore, the following actions and effects can be achieved.
(1) Surface contact and sealing in a ring shape with the breast main portion is possible and therefore airtight properties are improved and the negative pressure during expression of milk can be utilized efficiently.
(2) Since the breast main portion B is covered, than leaking of breast milk as described in relation to FIG. 8 can be prevented effectively.
(3) Since a ring-shaped surface contact is made with the breast main body B, the load applied to the breast main body B by the negative pressure during expression of milk can be distributed in a ring shape, and compared to the composition in FIG. 13, the whole of the breast main portion B of the user is not pulled inside the enlarged-diameter milk expressing section 22, and therefore the user does not suffer an uncomfortable sensation or pain.

Figure 12:
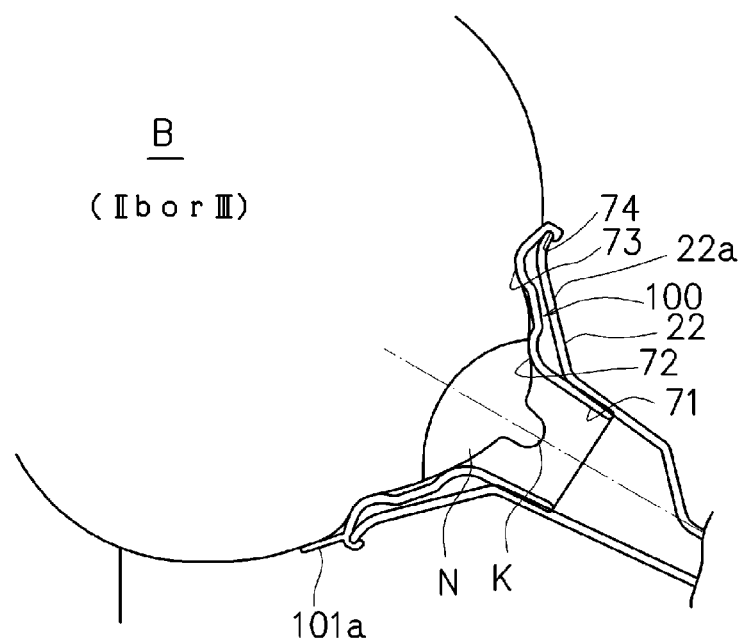
FIG. 12 is an enlarged cross-sectional diagram showing a relationship between the shock absorbing section and the user's breast and areola region during expression of milk, in the third embodiment shown in FIG. 11.

Here, outer edge cover section 101 does not necessarily have to be provided in a ring shape about the whole circumference of the shock absorbing section 100, as shown in FIG. 11, and may also be formed as a tongue-shaped cover section 101 a, for example, only on the lower edge of the shock absorbing section 100, as shown in FIG. 12.

More specifically, since leaking of breast milk during expression of milk often occurs due to milk dropping down around the lower edge or lower side of the breast main portion B, as described in relation to FIG. 8, in cases where an outer edge cover section 101 is provided, then leaking of breast milk can also be prevented effectively if a tongue-shaped cover section 101 a extending along the lower outer edge portion of the shock absorbing section is adopted so as to cover at least the region in question.

Furthermore, the tongue-shaped cover section 101 a may be formed separately from the enlarged-diameter milk expressing section 22, so as to be attachable to and detachable from the outer edge of the opening of the trumpet-shaped enlarged-diameter milk expressing section 22, whereby the cover section can be used appropriately in accordance with the breast size, breast shape and preferences of the user.

The present invention is not limited to the embodiments described above.

For example, the operating device 61 was described as a handle for manual operation, but may also be an electrically powered drive device which can be connected to the coupling section (member) 35.

Moreover, the mounting section 41 was described as being formed in a horizontal direction so as to face upwards, but may also be disposed in an obliquely inclined fashion following the air flow path 23, in which case, desirably, the air flow path 27 on the side of the negative pressure generating member 30 is formed at a position towards one side of the mounting section 41, in such a manner that breast milk does not flow down.

Furthermore, the individual compositions of each embodiment are not necessarily required in their entirety, and a portion thereof can be omitted, in which case it is possible to adopt a combination of different compositions by combining other compositions which are not illustrated, or to use the compositions of the embodiments in a combined fashion.

REFERENCE SIGNS LIST 11 accommodating vessel
20 breast pump
21 (breast pump) main body
22 enlarged-diameter milk expressing section
30 negative pressure generating member
31 (first) wall section
32 deforming section (second wall section)
33 bottom surface section
35 coupling section (member)
61 operating section (handle)
70, 80, 90, 100 shock absorbing section

The invention claimed is:
1. A breast pump, comprising:
an accommodating vessel for collecting breast milk;
a breast pump main body which is attached to and detached from the accommodating vessel and which generates a negative pressure for expressing milk; and
an enlarged-diameter milk expressing section which is provided on the breast pump main body and has an enlarged diameter in order to abut against a breast of a user, wherein
a shock absorbing section is disposed attachably and detachably with respect to the enlarged-diameter milk expressing section, the shock absorbing section being devised in such a manner that at least a portion thereof abuts against a breast of a user by being formed in a substantially circular trumpet shape following an opening section of the enlarged-diameter milk expressing section, and the shock absorbing section comprises:
a through hole, in a central portion thereof, exposing a nipple of a breast of a user in a state where the breast of the user is abutted against the enlarged-diameter milk expressing section;
an areola abutting section which is a protrusion-shaped or concentric circle-shaped projecting section provided at a position in the vicinity of and on the outer side of the through hole and which abuts against the areola of the user; and
a breast tight contact section which
is a longitudinal oval-shaped projecting section arranged lengthwise in a gravitational force direction,
is provided in a position on the outer side of the areola abutting section, and makes tight contact with the breast of the user,
wherein the shock absorbing section made of an elastic material has an outer edge cover section which extends radially outward from an engagement point where the enlarged-diameter milk expressing section is engaged with the shock absorbing section at a terminal outward end of the enlarged-diameter milk expressing section, and in cross section, the cover section extends substantially in a linear direction from the engagement point towards a terminal end of the cover section and extends from the engagement point substantially in a same direction as the enlarged-diameter milk expressing section in a non-used state.

2. The breast pump according to claim 1, wherein the shock absorbing section has a substantially longitudinally elliptical trumpet shape following an opening section of the enlarged-diameter milk expressing section.

3. The breast pump according to claim 1, wherein on the shock absorbing section a cover section is provided which extends on the outer side at least along a lower side outer edge portion of the shock absorbing section.

4. The breast pump according to claim 3, wherein on the shock absorbing section a cover portion is provided which extends in a ring shape along the outer edge portion.

5. The breast pump according to claim 1, wherein the areola abutting section is constituted by projections which abut against a plurality of locations on the areola of the user, in the vicinity of and on the outer side of the through hole.

6. The breast pump according to claim 2, wherein the areola abutting section is constituted by projections which abut against a plurality of locations on the areola of the user, in the vicinity of and on the outer side of the through hole.

7. The breast pump according to claim 3, wherein the areola abutting section is constituted by projections which abut against a plurality of locations on the areola of the user, in the vicinity of and on the outer side of the through hole.

8. The breast pump according to claim 4, wherein the areola abutting section is constituted by projections which abut against a plurality of locations on the areola of the user, in the vicinity of and on the outer side of the through hole.

9. The breast pump according to claim 2, wherein on the shock absorbing section a cover section is provided which extends on the outer side at least along a lower side outer edge portion of the shock absorbing section.

10. The breast pump according to claim 1, wherein the breast tight contact section is a longitudinal oval-shaped projecting section arranged lengthwise in a direction perpendicular to a pivot axis of a pump handle.

11. A breast pump, comprising:
an accommodating vessel for collecting breast milk;
a breast pump main body which is attached to and detached from the accommodating vessel and which generates a negative pressure for expressing milk; and
an enlarged-diameter milk expressing section which is provided on the breast pump main body and has an enlarged diameter in order to abut against a breast of a user, wherein
a shock absorbing section is disposed attachably and detachably with respect to the enlarged-diameter milk expressing section, the shock absorbing section being devised in such a manner that at least a portion thereof abuts against a breast of a user by being formed in a substantially circular trumpet shape following an opening section of the enlarged-diameter milk expressing section, and
the shock absorbing section including
a through hole, in a central portion thereof, exposing a nipple of the breast of the user in a state where the breast of the user is abutted against the enlarged-diameter milk expressing section,
an areola abutting section which is a protrusion-shaped or concentric circle-shaped projecting section provided at a position in a vicinity of and on an outer side of the through hole and which abuts against the areola of the user,
a breast tight contact section which is an oval-shaped projecting section provided in a position on the an outer side of the areola abutting section and which makes tight contact with the breast of the user, and
the shock absorbing section made of an elastic material having an outer edge cover section which extends radially outward from an engagement point where the enlarged-diameter milk expressing section is engaged with the shock absorbing section at a terminal outward end of the enlarged-diameter milk expressing section, wherein in cross section, the cover section extends substantially in a linear direction from the engagement point towards a terminal end of the cover section and extends from the engagement point substantially in a same direction as the enlarged-diameter milk expressing section in a non-used state.

12. The breast pump according to claim 11, the outer edge cover section is provided, in a ring shape, entirely on an entire circumference of the shock absorbing section.

13. The breast pump according to claim 11, the outer edge cover section is provided on a partial circumference of the shock absorbing section.

14. The breast pump according to claim 13, the outer edge cover section is in a tongue-shape.

15. The breast pump according to claim 11, wherein the cover section is configured for extending radially outward from the engagement point along the breast of the user in a used state.

16. The breast pump according to claim 11, wherein the breast tight contact section is a longitudinal oval-shaped projecting section arranged lengthwise in a direction perpendicular to a pivot axis of a pump handle.

* * * * *